United States Patent [19]

Arai et al.

[11] Patent Number: 5,391,677
[45] Date of Patent: Feb. 21, 1995

[54] ACRYLIC-FUNCTIONAL ORGANOPOLYSILOXANE AND METHOD FOR THE PREPARATION THEREOF

[75] Inventors: Masatoshi Arai; Takafumi Sakamoto; Kazutoshi Fujioka, all of Gunma, Japan

[73] Assignee: Shin-Etsu Chemical Co., Ltd., Tokyo, Japan

[21] Appl. No.: 105,164

[22] Filed: Aug. 12, 1993

Related U.S. Application Data

[63] Continuation-in-part of Ser. No. 917,178, Jul. 23, 1992, abandoned.

[30] Foreign Application Priority Data

Jul. 23, 1991 [JP] Japan .................................. 3-206586

[51] Int. Cl.$^6$ .............................................. C08G 77/40
[52] U.S. Cl. .......................................... 528/18; 528/32; 528/34; 556/440
[58] Field of Search ............... 528/18, 34, 32; 556/440

[56] References Cited

U.S. PATENT DOCUMENTS

| | | | |
|---|---|---|---|
| 3,427,337 | 2/1969 | Miller et al. | 556/440 |
| 3,878,263 | 4/1975 | Martin | 556/440 |
| 4,153,641 | 5/1979 | Deichert et al. | 556/440 |
| 4,387,240 | 6/1983 | Berg | 556/440 |
| 4,537,944 | 8/1985 | Imai et al. | 528/18 |
| 4,554,339 | 11/1985 | Hockemeyer et al. | 528/26 |
| 4,575,546 | 3/1986 | Klemarczyk et al. | 526/245 |
| 4,604,479 | 8/1986 | Ellis | 556/440 |
| 4,845,259 | 7/1989 | Arai et al. | 556/440 |

FOREIGN PATENT DOCUMENTS 276986 8/1988 European Pat. Off. .
2-304093 12/1990 Japan .

*Primary Examiner*—Ralph H. Dean
*Attorney, Agent, or Firm*—Millen, White, Zelano & Branigan

[57] ABSTRACT

A novel acrylic-functional organopolysiloxane is proposed which has a plural number of silicon-bonded (meth)acryloxyalkyl groups at each molecular chain end along with one or more of silicon-bonded alkoxy groups. The organopolysiloxane exhibits high curability by the irradiation with ultraviolet light or dual curability either by the ultraviolet irradiation or by the dealcoholation condensation reaction in a moisture-containing atmosphere. The acrylic-functional organopolysiloxane is prepared by the dealcoholation condensation reaction between a starting organopolysiloxane having a plural number of silicon-bonded alkoxy groups at each molecular chain end and a (meth)acryloxyalkyl dimethyl silanol compound in the presence of a specific condensation catalyst which is a divalent tin compound such as tin (II) dioctoate promoting the dealcoholation condensation but suppressing the silanol condensation reaction between the moleculaes of the (meth)acryloxyalkyl dimethyl silanol compound.

16 Claims, 4 Drawing Sheets

FIG. I

ACRYLIC-FUNCTIONAL ORGANOPOLYSILOXANE AND METHOD FOR THE PREPARATION THEREOF

This is a continuation-in-part application U.S. patent application Ser. No. 07/917,178, filed Jul. 23, 1992, now abandoned.

BACKGROUND OF THE INVENTION

The present invention relates to a novel acrylic-functional organopolysiloxane and a method for the preparation thereof. More particularly, the invention relates to an organopolysiloxane having a plurality of (meth)acryloxy-substituted alkyl groups as the functional groups at the molecular chain ends and an efficient method for the synthetic preparation of such an acrylic-functional organopolysiloxane.

It is well known that a high molecular-weight organopolysiloxane can be converted into a silicone rubber elastomer having excellent heat and cold resistance, weatherability and electric properties by heating in the presence of an organic peroxide as a curing agent. It is also known that a high molecular-weight organopolysiloxane of a certain functional type can be cured into a rubbery elastomer by the irradiation with ultraviolet light in the presence of a photosensitizer.

The ultraviolet-curable organopolysiloxane compositions heretofore known include those in which the crosslinking reaction proceeds between a vinyl group-containing organopolysiloxane and a mercapto group-containing organopolysiloxane by the photochemically induced free-radical addition reaction (see, for example, Japanese Patent Publication No. 52-40334 and Japanese Patent Kokai No. 60-104158). The organopolysiloxane compositions of this type have a disadvantage that the application field thereof is very limited due to the unpleasant odor more or less emitted by the mercapto group-containing organopolysiloxane as is the case in any mercapto-containing organic compounds as well as the corrosiveness of the composition to the surface of a metallic article in contact therewith due to the mercapto groups.

Ultraviolet-curable organopolysiloxanes of another class include those comprising an organopolysiloxane having at least two acrylic groups in a molecule and a photosensitizer disclosed in, for example, Japanese Patent Publication No. 53-36515 and Japanese Patent Kokai No. 60-215009. Since these acrylic-functional organopolysiloxanes must have a linear molecular structure of a quite high molecular weight and the acrylic groups are bonded only to the terminals of the polymeric molecules in order to be able to give a rubbery elastomer by curing, it is a natural consequence that the number of the acrylic functional groups is relatively very small in the so large molecules so that the curability of the composition is usually low and the curing reaction sometimes does not proceed to completion, especially, in the surface layer due to the inhibiting effect of the atmospheric oxygen on the flee-radical reaction. This is the reason for the fact that utilization of the curing mechanism by the ultraviolet-induced addition reaction in the acrylic-functional groups is limited to certain resinous compositions in which a multiple number of the acrylic-functional groups can be introduced per molecule of the resinous organopolysiloxane having a branched molecular structure.

Japanese Patent Kokai No. 63-183911 discloses an ultraviolet-curable organopolysiloxane composition comprising an acrylic-terminated diorganopolysiloxane of a linear molecular structure and a photosensitizer, of which the acrylic functional groups are introduced into the terminals of the linear organopolysiloxane molecules by using an acryloxyalkyl-containing silanol compound. Although the organopolysiloxane composition of this type is capable of giving a rubbery elastomer by curing, such a composition is not suitable for industrialization because the process for the preparation of the acrylic-functional organopolysiloxane is very lengthy and complicated consequently resulting in an increase in the costs.

SUMMARY OF THE INVENTION

The present invention accordingly has an object to provide a novel acrylic-functional organopolysiloxane capable of giving a rubbery elastomer by the irradiation with ultraviolet light without the problems and disadvantages in the prior art acrylic-functional organopolysiloxanes as well as to provide a novel and efficient method for the preparation of such an acrylic-functional organopolysiloxane.

Thus, the novel acrylic-functional organopolysiloxane of the invention is a compound represented by the general formula

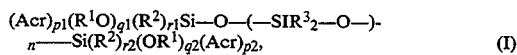

$$(Acr)_{p1}(R^1O)_{q1}(R^2)_{r1}Si-O-(-SiR^3{}_2-O-)_n-Si(R^2)_{r2}(OR^1)_{q2}(Acr)_{p2}, \quad (I)$$

in which each of $R^1$, $R^2$ and $R^3$ is, independently from the others, an unsubstituted or substituted monovalent hydrocarbon group, Acr is an acrylic-functional monovalent group or an ω-(meth)acryloxyalkyl dimethyl siloxy group represented by the general formula

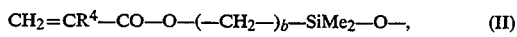

$$CH_2=CR^4-CO-O-(-CH_2-)_b-SiMe_2-O-, \quad (II)$$

$R^4$ being a hydrogen atom or a methyl group, Me being a methyl group and b being 1, 2 or 3, the subscript n is zero or a positive integer not exceeding 10,000, each of the subscripts p1 and p2 is 1, 2 or 3 and each of the subscripts q1, q2, r1 and r2 is zero, 1 or 2 or, in particular, p1 and p2 are each 2 or 3 and q1 and q2 are each not zero with the proviso that p1+q1+r1 is 3 and p2+q2+r2 is 3.

The above defined novel acrylic-functional organopolysiloxane can be prepared in a process comprising the step of: reacting an organopolysiloxane having at least one alkoxy group bonded to the terminal silicon atom at each molecular chain end represented by the general formula

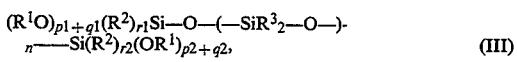

$$(R^1O)_{p1+q1}(R^2)_{r1}Si-O-(-SiR^3{}_2-O-)_n-Si(R^2)_{r2}(OR^1)_{p2+q2}, \quad (III)$$

in which each symbol has the same meaning as defined above, with an ω-(meth)acryloxyalkyl dimethyl silanol represented by the general formula

$$CH_2=CR^4-CO-O-(-CH_2-)_b-SiMe_2-OH, \quad (IV)$$

in which each symbol has the same meaning as defined above, in the presence of a divalent tin compound represented by the general formula $SnX_2$, in which X is a halogen atom, an alkoxy group or a carboxylic acid residue forming a tin salt, as a catalyst to effect the dealcoholation condensation reaction to form an alcohol of the formula $R^1OH$ as the condensation product.

DETAILED DESCRIPTION OF THE PREFERRED EMBODIMENTS

Figure 1:
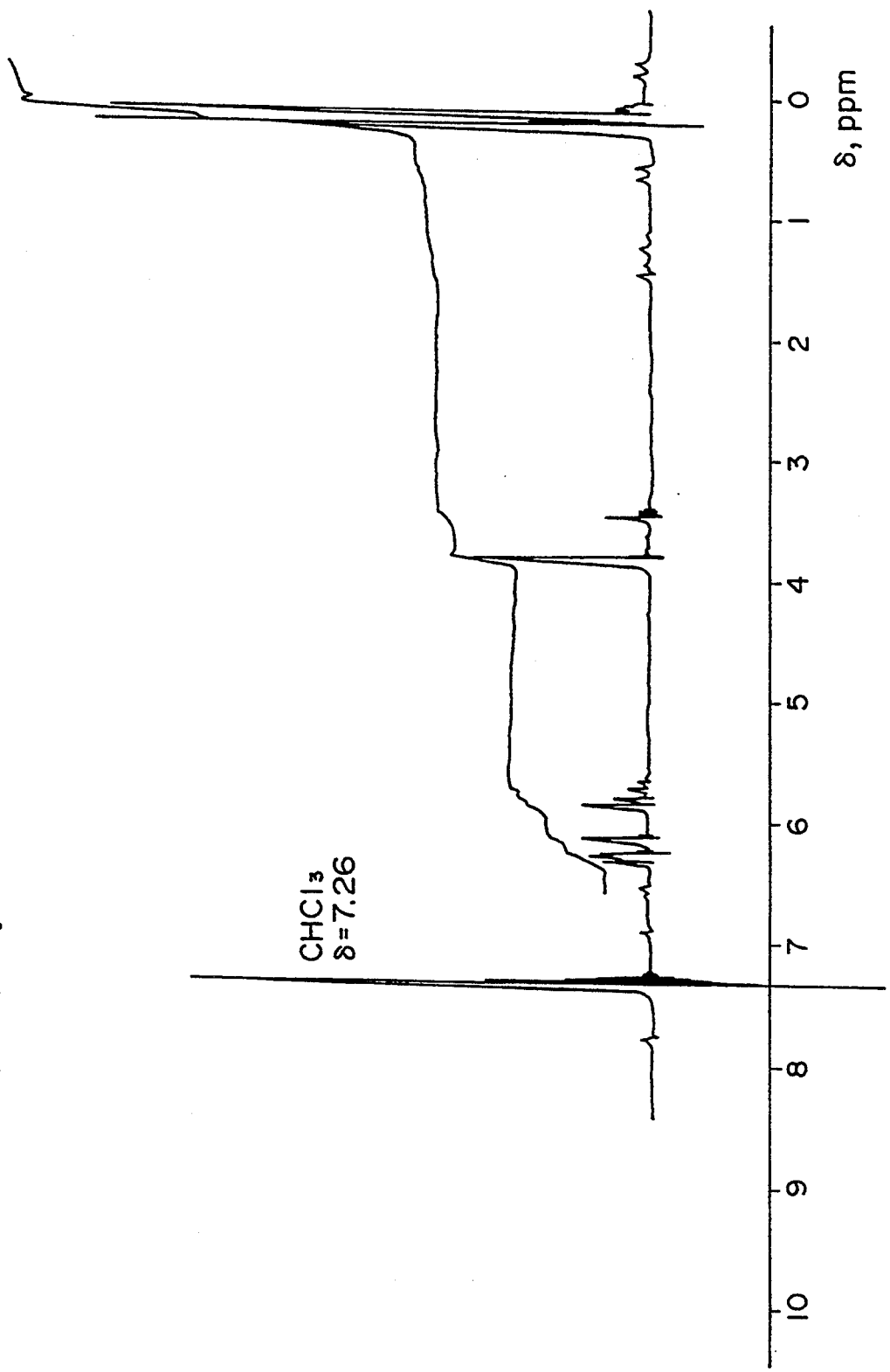
FIG. 1 is a nuclear magnetic resonance spectrum of the acrylic-functional organopolysiloxane of the present invention prepared in Example 1.

As is described above, the novel acrylic-functional organopolysiloxane of the invention is defined by the general formula (I), according to which each of the silicon atoms at the molecular chain ends of the polysiloxane structure has at least one or, preferably, 2 or 3 acrylic-functional organosiloxy groups of the general formula (II) bonded thereto, optionally, in combination with one or two alkoxy groups $R^1O$ when p1 or p2 is not 3. When the acrylic-functional organopolysiloxane has 2 or 3 acrylic functional groups at each molecular chain end, the curability of the organopolysiloxane by the irradiation with ultraviolet light can be greatly enhanced and, when the acrylic-functional organopolysiloxane has at least one acrylic functional group and at least one alkoxy group at each molecular chain end, the organopolysiloxane is imparted with dual curability both by the ultraviolet irradiation and by the condensation reaction in a moisture-containing atmosphere.

The above described acrylic-functional organopolysiloxane of the invention is highly curable by the irradiation with ultraviolet light to give a rubbery elastomer which exhibits firm adhesive bonding to the surface of a substrate of glass, metal, plastic and the like on which the organopolysiloxane is cured. When the organopolysiloxane has one or more of alkoxy groups at each molecular chain end, furthermore, the organopolysiloxane can be used as a modifying agent or surface-treatment agent of inorganic or organic materials or as a base material of silicone resins and silicone rubbers by virtue of the reactivity of the alkoxy groups to pertain to a dealcoholation condensation reaction. Advantageously, the organopolysiloxane of the invention is absolutely free from the problems of unpleasant odor and corrosiveness against metals as is the case with a mercapto-containing compound. Furthermore, the curing reaction of the inventive organopolysiloxane is not affected by the inhibiting effect of the atmospheric oxygen.

The method of the invention for the preparation of this novel acrylic-functional organopolysiloxane is briefly described above. It is a quite unexpected discovery that the dealcoholation condensation reaction between the alkoxy-terminated diorganopolysiloxane of the general formula (III) and the acrylic-functional silanolic compound of the general formula (IV) can proceed very efficiently when a divalent tin compound $SnX_2$ is used as the catalyst. When this specific tin compound is used as the catalyst for the condensation reaction, the otherwise unavoidable silanol condensation reaction between the molecules of the silanol compound of the formula (IV) proceeds only at a very low velocity while the dealcoholation condensation reaction between the alkoxy groups at the molecular chain ends of the organopolysiloxane and the silanolic hydroxy groups in the acrylic-functional silanol compound is greatly promoted by the catalytic activity.

In the above given general formula (I) representing the acrylic-functional organopolysiloxane of the invention, the symbols $R^1$, $R^2$ and $R^3$ each denote, independently from the others, an unsubstituted or substituted monovalent hydrocarbon group having 1 to 10 or, in particular, 1 to 8 carbon atoms exemplified by alkyl groups such as methyl, ethyl, propyl and butyl groups, alkenyl groups such as vinyl and allyl groups and aryl groups such as phenyl and tolyl groups as well as chloromethyl group, 3,3,3-trifluoropropyl group and the like obtained by replacing a part or all of the hydrogen atoms in the above named unsubstituted hydrocarbon groups with substituents such as halogen atoms. The symbol $R^4$ denotes a hydrogen atom or a methyl group so that the terminal functional group is an acryloxy group or a methacryloxy group, respectively. The subscript n is a determinant value for the degree of polymerization of the organopolysiloxane molecule and has a value of zero or a positive integer not exceeding 10,000. The subscripts p1, q1, r1, p2, q2 and r2 each have a value defined before. Since p1 and p2 are each not zero by definition, each molecule of the organopolysiloxane has at least one functional group of the symbol Acr at each molecular chain end. When q1 and q2 are each zero, in particular, p1 and p2 are each 2 or 3 and, when p1 and p2 are each equal to 1, q1 and q2 are each not zero.

Examples of the inventive organopolysiloxane represented by the general formula (I) include those expressed by the following structural formulas, in which Me is a methyl group:

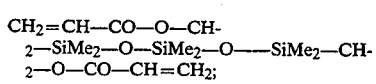

CH$_2$=CH—CO—O—CH-
2—SiMe$_2$—O—SiMe$_2$—O——SiMe$_2$—CH-
2—O—CO—CH=CH$_2$;

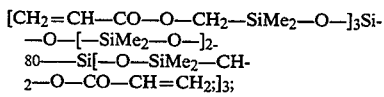

[CH$_2$=CH—CO—O—CH$_2$—SiMe$_2$—O—]$_3$Si-
—O—[—SiMe$_2$—O—]$_2$-
80——Si[—O—SiMe$_2$—CH-
2—O—CO—CH=CH$_2$]$_3$;

and

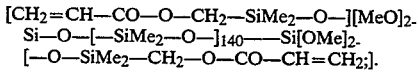

[CH$_2$=CH—CO—O—CH$_2$—SiMe$_2$—O—][MeO]$_2$-
Si—O—[—SiMe$_2$—O—]$_{140}$——Si[OMe]$_2$-
[—O—SiMe$_2$—CH$_2$—O—CO—CH=CH$_2$].

As is described above, the above defined acrylic-functional organopolysiloxane of the general formula (I) can be prepared by the dealcoholation condensation reaction between an alkoxy-terminated organopolysiloxane of the general formula (III) and the acrylic-functional dimethyl silanol compound of the general formula (IV) in the presence of a specific divalent tin compound as a catalyst. Examples of the alkoxy-terminated organopolysiloxane of the general formula (III) include:

1,3-dimethoxy-1,1,3,3-tetramethyl disiloxane;
1,3-dimethoxy-1,3-dimethyl-1,3-diphenyl disiloxane;
1,3-dimethoxy-1,1,3,3-tetraphenyl disiloxane;
1,1,3,3-tetramethoxy-1,3-dimethyl disiloxane;
1-methoxy-3-ethoxy-1,1,3,3-tetramethyl disiloxane;
1-methoxy-3-ethoxy-1,3-dimethyl-1,3-diphenyl disiloxane;
1-methoxy-3-ethoxy-1,1,3,3-tetraphenyl disiloxane;
1,1,3,3-tetraethoxy-1,3-dimethyl disiloxane;
1,5-dimethoxy-1,1,3,3,5,5-hexamethyl trisiloxane; and
1-methoxy-5-ethoxy-1,1,3,3,5,5-hexamethyl trisiloxane;

as well as those expressed by the following average formulas, in which Me is a methyl group, Et is an ethyl group and Ph is a phenyl group:

MeO—[—SiMePh—O—]$_6$—[—SiMe$_2$—O—]$_3$—Me;
MeO—[—SiMePh—O—]$_6$—[—SiMe$_2$—O—]$_3$—Me;
MeO—[—SiMe$_2$—O—]$_{200}$—Me;
MeO—[—SiMePh—O—]$_{200}$—[—SiMe$_2$—O—]$_{800}$—Me;
EtO—[—SiMe$_2$—O—]$_{200}$—Me;
EtO—[—SiMePh—O—]$_{200}$—[—SiMe$_2$—O—]$_{800}$—Me; and
(MeO)$_3$Si—O—[—SiMe$_2$O—]$_{200}$—Si(OMe)$_3$.

Examples of the acrylic-functional dimethyl silanol compound of the general formula (IV) include: acryloxymethyl dimethyl silanol; 3-acryloxypropyl dimethyl silanol; methacryloxymethyl dimethyl silanol and 3-methacryloxypropyl dimethyl silanol, though not particularly limited thereto.

The divalent tin compound used as the catalyst for the dealcoholation condensation reaction between the above described alkoxy-terminated organopolysiloxane of the general formula (III) and the acrylic-functional dimethyl silanol compound of the general formula (IV) is represented by the general formula SnX$_2$, in which X is a halogen atom, an alkoxy group or a carboxylic acid residue forming a tin salt. Examples of the divalent tin compound suitable as the catalyst include tin (II) chloride, tin (II) bromide, tin (II) iodide, tin (II) acetate, tin (II) oxalate, tin (II) dioctoate, tin dimethoxide, tin (II) hexadecanoate and the like, though not particularly limited thereto.

The dealcoholation condensation reaction mentioned above can be performed by mixing the alkoxy-terminated organopolysiloxane of the general formula (III) and the acrylic-functional dimethyl silanol compound of the general formula (IV) in an approximately stoichiometric proportion together with the divalent tin compound as the catalyst and heating the mixture at a temperature in the range from room temperature to 120° C. or, preferably, from 20° to 70° C. under agitation for a length of time of one hours to 48 hours so that the condensation reaction proceeds to form an alcohol of the formula R$^1$OH as a by-product of the dealcoholation condensation reaction. It is optional that the reaction mixture is diluted with an organic solvent such as benzene, toluene, xylene and the like. After completion of the reaction, the organic solvent and the by-product alcohol can be readily removed from the reaction mixture by distillation but the reaction mixture still containing the organic solvent and/or the by-product alcohol can sometimes be used as such without removal thereof depending on the intended applications.

The amount of the divalent tin compound as the catalyst naturally depends on the desired reaction velocity of the condensation reaction but it is usually in the range from 10 to 10,000 ppm by weight based on the amount of the alkoxy-terminated organopolysiloxane. The amount of the acrylic-functional dimethyl silanol compound is selected depending on the extent of substitution of the alkoxy-functional dimethyl siloxy group of the general formula (II) for the alkoxy groups in the alkoxy-terminated organopolysiloxane. When each of the molecular chain ends of the alkoxy-terminated organopolysiloxane is blocked with a trialkoxysilyl group and all of the alkoxy groups are desired to be replaced with the acrylic-functional dimethyl siloxy groups, for example, the amount of the acrylic-functional dimethyl silanol compound must be at least 6 moles per mole of the alkoxy-terminated organopolysiloxane. When it is desired to introduce a single acrylic-functional group into each of the molecular chain ends, the amount of the (meth)acryloxyalkyl dimethyl silanol compound of the general formula (IV) should be 2 moles or somewhat larger per mole of the starting alkoxy-terminated organopolysiloxane of the general formula (III).

As is mentioned before, the very scope of the inventive method consists in the use of a very specific catalyst compound which exhibits a selective activity for the condensation reaction to form a siloxane linkage promoting only the dealcoholation reaction between silicon-bonded alkoxy groups and the silicon-bonded hydroxy groups and not promoting the silanol condensation reaction between the silicon-bonded hydroxy groups.

In the following, the inventive acrylic-functional organopolysiloxane and the method for the preparation thereof are described in more detail by way of examples.

Example 1

Figure 2:
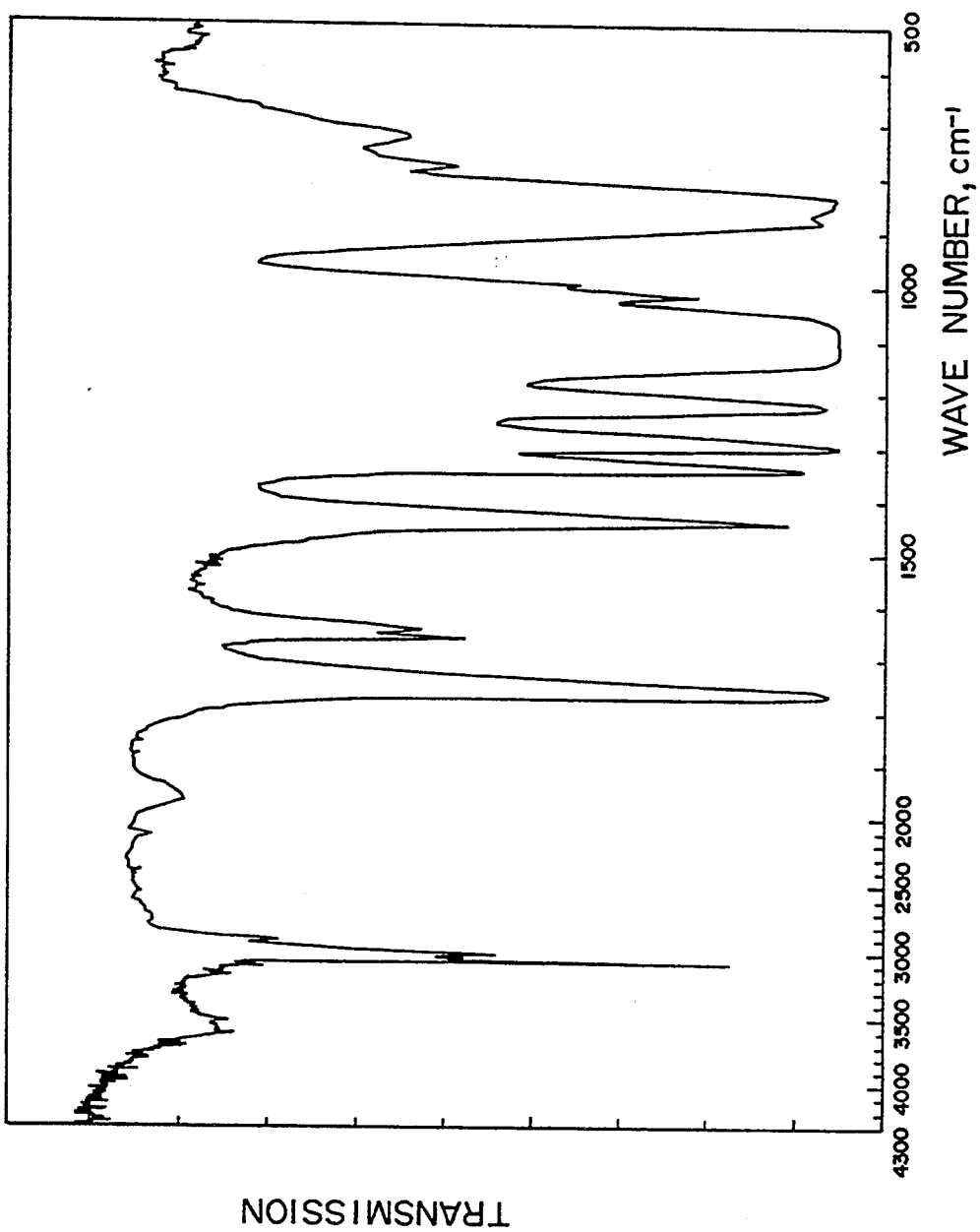
FIGS. 2, 3 and 4 are each an infrared absorption spectrum of the acrylic-functional organopolysiloxanes of the present invention prepared in Examples 1, 2 and 3, respectively.

Into a four-necked round-bottom flask of 1 liter capacity equipped with a thermometer, reflux condenser, dropping funnel and stirrer were introduced 388.8 g (4 moles) of 1,3-dimethoxy-1,1,3,3-tetramethyl disiloxane and 0.39 g of tin (II) dioctoate to form a reaction mixture by agitation and 320 g (2 moles) of acryloxymethyl dimethyl silanol were added dropwise thereinto followed by continued agitation of the reaction mixture at room temperature for 12 hours. After completion of this reaction time, the reaction mixture was subjected to distillation to obtain 580 g of a fraction boiling at about 185° C. as the product. The results of the analysis of this product including the nuclear magnetic resonance spectrometry and infrared absorption spectrophotometry to give the spectra shown in FIGS. 1 and 2, respectively, as well as the gas chromatographic-mass spectrometric analysis to give a molecular weight of 322 supported that this product was 1-acryloxymethyl-5-methoxy-1,1,3,3,5,5-hexamethyl trisiloxane. The above mentioned yield of the product corresponds to about 90% of the theoretical value.

The same experimental procedure as above was repeated except that, instead of agitating for 12 hours at room temperature, the reaction mixture was agitated for 1 hour at 50° C. The results of the analysis indicated that the thus obtained product was identical with that obtained by the reaction at room temperature. The yield of the product was 88% of the theoretical value.

Example 2

Figure 3:
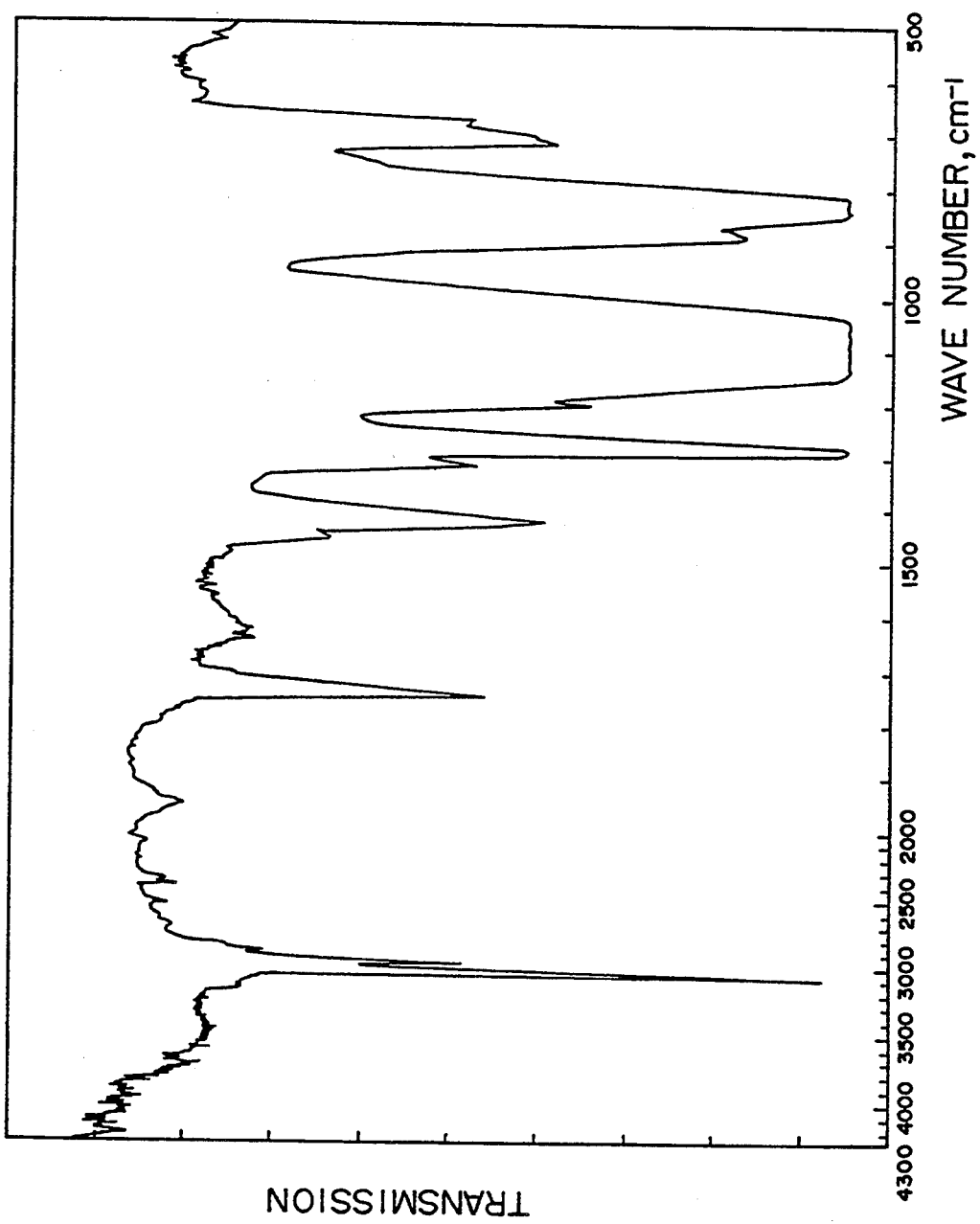

Into the same reaction flask as used in Example 1 were introduced 500 g of a trimethoxysilyl-terminated dimethyl polysiloxane (molecular weight 10618) having a viscosity of 1300 centistokes at 25° C., of which the average number of silicon atoms per molecule was 282, containing 0.135 mole of methoxy groups and 0.50 g of tin (II) dioctoate to form a reaction mixture, into which 21.6 g (0.135 mole) of acryloxymethyl dimethyl silanol were added dropwise under agitation and the mixture was continuedly agitated for 48 hours at room temperature. After the end of this reaction time, the reaction mixture was freed from methyl alcohol as the by-product by heating at 40° C. under a pressure of 50 mmHg to leave 466 g of a clear, colorless and viscous fluid having a viscosity of 1600 centistokes at 25° C. The results of the analysis of this product including the infrared absorption spectrophotometry to give the spectrum shown in FIG. 3 supported that this product was expressed by the average formula

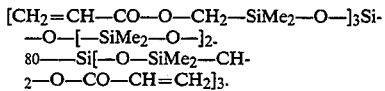

The above mentioned yield of the product corresponds to about 90% of the theoretical value.

This product was admixed with 3% by weight of a photosensitizer (Irgacure 184, a product by Ciba-Geigy Co.) and the mixture was irradiated with ultraviolet light to give a cured rubbery elastomer. A comparative irradiation test with the trimethoxysilyl-terminated dimethyl polysiloxane used as the starting material in the above described preparation failed to give a cured rubbery elastomer.

Example 3

Figure 4:
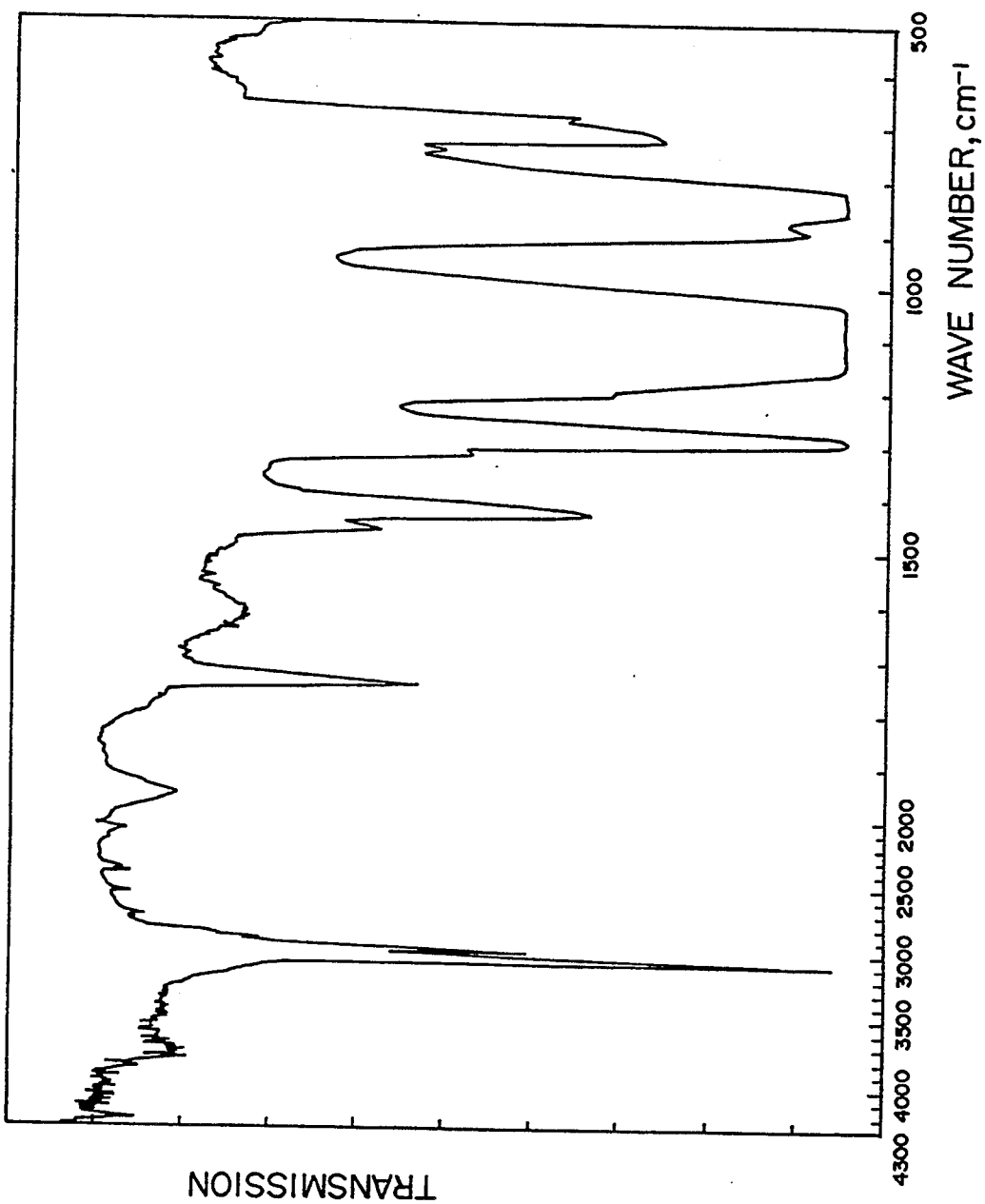

The experimental procedure was substantially the same as in Example 2 except that the amount of the acryloxymethyl dimethyl silanol was decreased to 7.2 g (0.045 mole). The yield of the clear and colorless liquid product having a viscosity of 1500 centistokes at 25° C. was 455 g. The results of the analysis of this product including the infrared absorption spectrophotometry to give the spectrum shown in FIG. 4 supported that this product was expressed by the average formula

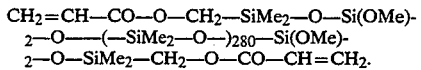

The above mentioned yield of the product corresponds to about 90% of the theoretical value.

This product was subjected to the ultraviolet irradiation test in the same manner as in Example 2 with admixture of the same photosensitizer to give a cured rubbery elastomer. Further, this product was admixed with 1% by weight of dibutyl tin dimethoxide and the mixture was kept standing for 72 hours in an atmosphere of 55% relative humidity at 22° C. to find that it was converted into a cured rubbery elastomer. On the other hand, the starting trimethoxysilyl-terminated dimethyl polysiloxane with admixture of dibutyl tin dimethoxide failed to give a cured rubbery elastomer after 72 hours of standing.

Example 4

A reaction mixture was prepared in the same formulation as in Example 2 excepting a decrease of the acryloxymethyl dimethyl silanol from 21.6 g to 7.2 g and the reaction mixture was agitated for 24 hours at room temperature. The acryloxy-functional organopolysiloxane obtained in this manner had a viscosity of 1600 centistokes at 25° C.

The acryloxy-functional organopolysiloxane thus obtained was admixed with 2% by weight of 2,2-diethoxy acetophenone as a photosensitizer and the composition was irradiated with ultraviolet light in a dose of 1500 mJ/cm² so that the composition was converted into a cured rubbery elastomer. Further, the acryloxy-functional organopolysiloxane was admixed with 0.5% by weight of dibutyl tin dimethoxide and the composition was kept standing for 72 hours in an atmosphere of 55% relative humidity at 20° C. to be converted also into a cured rubbery elastomer.

For comparison, the same experimental procedure as above was repeated excepting replacement of the tin (II) dioctoate with the same amount of titanium tetra(isopropoxide) or sulfuric acid. The thus obtained reaction products had a viscosity of 13,500 centistokes or 1500 centistokes at 25° C., respectively. These comparative organopolysiloxanes were each subjected to the same curing tests as above to find that they failed to be cured by the ultraviolet irradiation although their curing behavior with admixture of dibutyl tin dimethoxide as a condensation catalyst was substantially the same as in the inventive acryloxy-functional organopolysiloxane.

What is claimed is:

1. An acrylic-functional organopolysiloxane which is a compound represented by the general formula

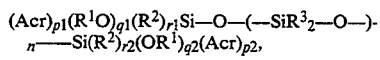

in which each of $R^1$, $R^2$ and $R^3$ is, independently from the others, an unsubstituted or substituted monovalent hydrocarbon group, Acr is an ω-(meth) acryloxyalkyl dimethyl siloxy group represented by the general formula

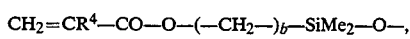

$R^4$ being a hydrogen atom or a methyl group, Me being a methyl group and b being 1, 2 or 3, the subscript n is zero or a positive integer not exceeding 10,000, each of the subscripts p1 and p2 is 1 or 2 and each of the subscripts r1 and r2 is zero or 1 and each of the subscripts q1 and q2 is 1 or 2, with the proviso that p1+q1+r1 is 3 and p2+q2+r2 is 3.

2. The acrylic-functional organopolysiloxane as claimed in claim 1 in which the subscripts p 1 and p2 are each 2.

3. The acrylic-functional organopolysiloxane as claimed in claim 2 in which the subscripts q1 and q2 are each 1 when p1 and p2 are each 2.

4. An acrylic-functional organopolysiloxane according to claim 1, wherein $R^1$, $R^2$ and $R^3$ are each an unsubstituted or halogen-substituted monovalent hydrocarbon group having 1–10 carbon atoms.

5. An acrylic-functional organopolysiloxane according to claim 4, wherein $R^1$, $R^2$ and $R^3$ are each independently methyl, ethyl, propyl, butyl, vinyl, allyl, phenyl, tolyl, chloromethyl or 3,3,3-trifluoropropyl.

6. An acrylic-functional organopolysiloxane according to claims 4, wherein $R^1$ is an alkyl group of 1–10 carbon atoms.

7. A method for the preparation of an acrylic-functional organopolysiloxane which is a compound represented by the general formula

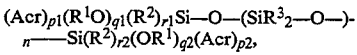

in which each of $R^1$, $R^2$ and $R^3$ is, independently from the others, an unsubstituted or substituted monovalent hydrocarbon group, Acr is an ω-(meth)acryloxyalkyl dimethyl siloxy group represented by the general formula

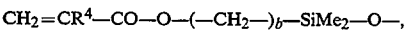

$R^4$ being a hydrogen atom or a methyl group, Me being a methyl group and b being 1, 2 or 3, the subscript n is zero or a positive integer not exceeding 10,000, each of the subscripts p1 and p2 is 1, 2 or 3 and each of the subscripts q1, q2, r1 and r2 is zero, 1 or 2 with the proviso that p1+q1+r1 is 3 and p2+q2+r2 is 3, which comprises the step of:

mixing (a) an organopolysiloxane having at least one alkoxy group bonded to the terminal silicon atom at each molecular chain end represented by the general formula

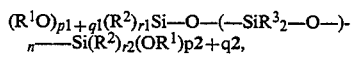

in which each symbol has the same meaning as defined above, with (b) an ω-(meth)acryloxyalkyl dimethyl silanol represented by the general formula

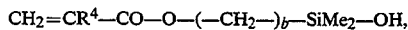

in which each symbol has the same meaning as defined above, in the presence of (c) a divalent tin compound represented by the general formula $SnX_2$, in which X is a halogen atom, an alkoxy group or a carboxylic acid residue forming a tin (II) salt.

8. The method for the preparation of an acrylic-functional organopolysiloxane as claimed in claim 7 in which the group X is a carboxylic acid residue forming a tin (II) salt.

9. The method for the preparation of an acrylic-functional organopolysiloxane as claimed in claim 8 in which the carboxylic acid residue forming a tin (II) salt denoted by X is an octoyloxy group forming tin (II) dioctoate.

10. The method for the preparation of an acrylic-functional organopolysiloxane as claimed in claim 7 in which the amount of the divalent tin compound (c) is in the range from 10 to 10,000 ppm by weight based on the amount of alkoxy-terminated organopolysiloxane (a).

11. A method according to claim 7, wherein $R^1$, $R^2$ and $R^3$ are each an unsubstituted or halogen-substituted monovalent hydrocarbon group having 1–10 carbon atoms.

12. A method according to claim 11, wherein $R^1$, $R^2$ and $R^3$ are each independently methyl, ethyl, propyl, butyl, vinyl, allyl, phenyl, tolyl, chloromethyl or 3,3,3-trifluoropropyl.

13. A method according to claim 7, wherein said organopolysiloxane having at least one alkoxy group bonded to the terminal silicon atom at each molecular chain end is 1,3-dimethoxy-1,1,3,3-tetramethyl disiloxane;
1,3-dimethoxy-1,3-dimethyl-1,3-diphenyl disiloxane;
1,3-dimethoxy-1,1,3,3-tetraphenyl disiloxane;
1,1,3,3-tetramethoxy-1,3-dimethyl disiloxane;
1-methoxy-3-ethoxy-1,1,3,3-tetramethyl disiloxane;
1-methoxy-3-ethoxy-1,3-dimethyl-1,3-diphenyl disiloxane;
1-methoxy-3-ethoxy-1,1,3,3-tetraphenyl disiloxane;
1,1,3,3-tetraethoxy-1,3-dimethyl disiloxane;
1,5-dimethoxy-1,1,3,3,5,5-hexamethyl trisiloxane; or
1-methoxy-5-ethoxy-1,1,3,3,5,5-hexamethyl trisiloxane.

14. A method according to claim 7, wherein said ω-(meth) acryloxyalkyl dimethyl silanol is acryloxymethyl dimethyl silanol; 3-acryloxypropyl dimethyl silanol; methacryloxymethyl dimethyl silanol or 3-methacryloxypropyl dimethyl silanol.

15. A method according to claim 7, wherein said divalent tin compound is tin (II) chloride, tin (II) bromide, tin (II) iodide, tin (II) acetate, tin (II) oxalate, tin (II)dioctoate, tin dimethoxide, or tin (II) hexadecanoate.

16. A method according to claim 7, wherein p1 and p2 are each 1 or 2, r1 and r2 are each 0 or 1, and q1 and q2 are each 1 or 2.

* * * * *